(12) United States Patent
Barker et al.

(10) Patent No.: US 6,214,624 B1
(45) Date of Patent: Apr. 10, 2001

(54) USE OF PERFLUOROCARBONS AS TRACERS IN CHEMICAL COMPOSITIONS

(75) Inventors: David Allen Barker, Cypress; Thomas Clayton Forschner, Richmond; Randall Lee Shearer, Houston, all of TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 08/234,495

(22) Filed: Apr. 28, 1994

Related U.S. Application Data

(60) Continuation of application No. 08/154,830, filed on Nov. 19, 1993, now abandoned, which is a division of application No. 07/999,446, filed on Dec. 31, 1992, now abandoned.

(51) Int. Cl.[7] .......................... G01N 37/00; G01N 31/00; G01N 33/00
(52) U.S. Cl. ................. 436/8; 436/56; 436/124; 436/125
(58) Field of Search .................. 436/8, 56, 124, 436/125

(56) References Cited

U.S. PATENT DOCUMENTS

| | | | |
|---|---|---|---|
| 4,141,692 | 2/1979 | Keller | 44/59 |
| 4,256,038 | 3/1981 | Dietz et al. | 102/202.5 |
| 4,445,364 | 5/1984 | Stieff et al. | 73/40.7 |
| 4,493,207 | 1/1985 | Dempsey | 73/40.7 |
| 4,520,109 | 5/1985 | Simmonds et al. | 436/56 |
| 4,709,577 | 12/1987 | Thompson | 73/40.7 |
| 4,725,551 | 2/1988 | Thompson | 436/3 |

OTHER PUBLICATIONS

Begley et al. "Femtogram Detection of PFC Tracers . . . " Journal of Chromatography, 445(1988) 119–128.*

* cited by examiner

*Primary Examiner*—Lynette R. F. Smith

(57) ABSTRACT

The present invention is directed to tracer-containing chemical compositions and to the use of at least one perfluorocarbon tracer in such compositions to provide a means of identifying and quantitatively analyzing such compositions.

9 Claims, 1 Drawing Sheet

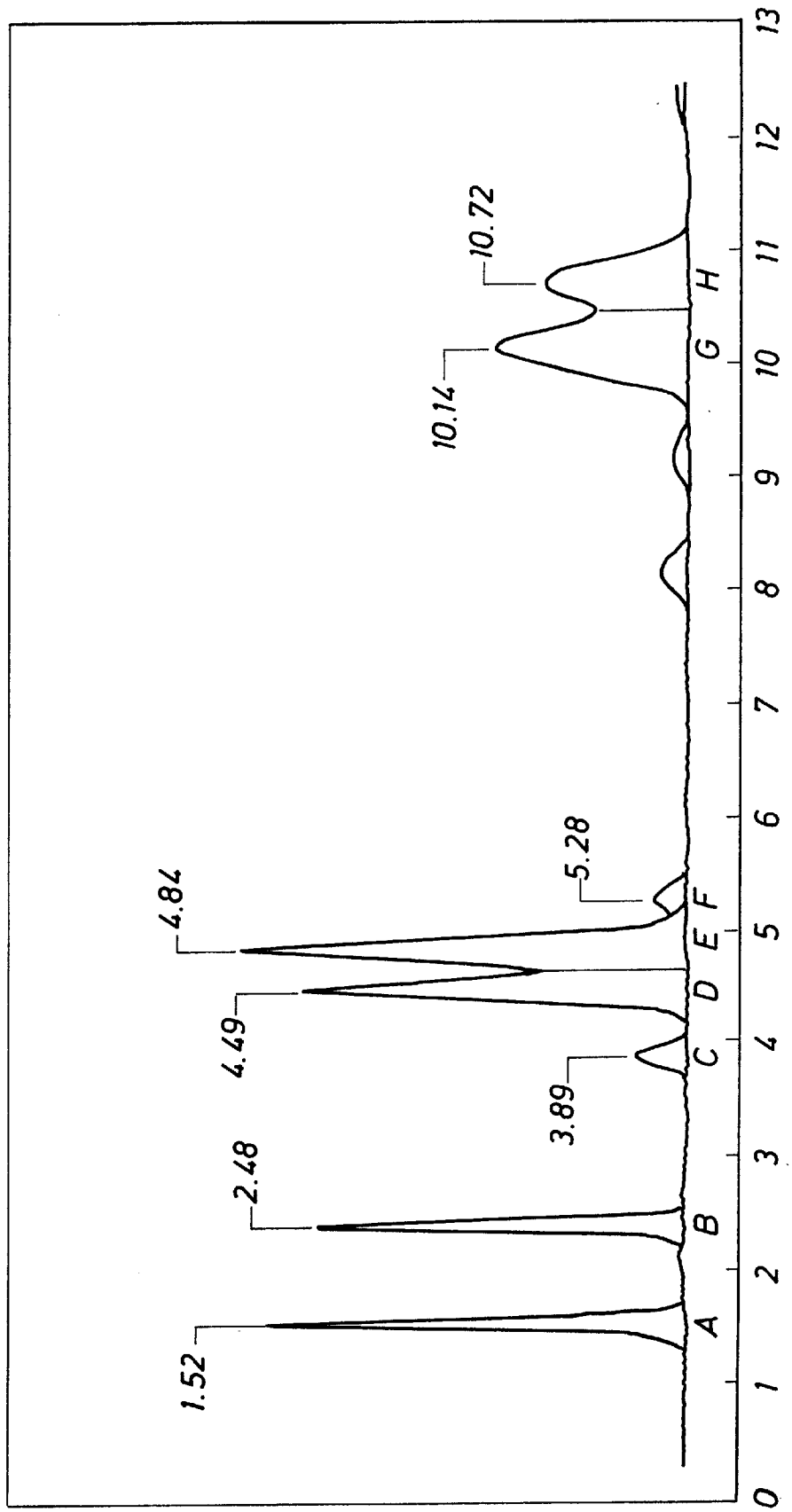

USE OF PERFLUOROCARBONS AS TRACERS IN CHEMICAL COMPOSITIONS

This is a continuation of application Ser. No. 08/154,830, filed Nov. 19, 1993 now abandoned which is a divisional of Ser. No. 07/999,446 filed Dec. 31, 1992, now abandoned.

BACKGROUND OF THE INVENTION

1. Field of the Invention

The present invention relates to tracer-containing chemical compositions. The present invention further relates to a process for using perfluorocarbon tracers in such compositions as a means of determining the possible adulteration of chemical compositions by identifying and quantitatively determining the amounts of such tracers present in such compositions.

2. Description of the Prior Art

The petrochemical industry has traditionally been faced with the problem of distinctively characterizing products for identification purposes. This characterization has typically been accomplished by using various labels or tags. Chlorohydrocarbons have been used to tag hydrocarbon fuel compositions but require that large amounts, from 0.01 mg/l to 10 mg/l, be incorporated for detection. See U.S. Pat. No. 4,141,692. Chlorofluorocarbons, which offer the advantage of having a lower limit of detection, have also been used as tracers. Both chlorohydrocarbons and chlorofluorocarbons are unacceptable though since each is known to deplete the ozone.

Dyes have also been used to tag products such as gasolines, but have proven ineffective for tagging products with a high degree of color. In addition, dyes generally have a high boiling point which makes them unsuitable for many applications.

Radioactive materials function as effective tags since they are detected using noninvasive procedures. Although isotopically labelled compounds are commercially available, the quantity of tracer needed makes them cost prohibitive. In addition, such materials cannot be readily used in commercial products.

It has now been found that very small amounts of one or more perfluorocarbon compounds can be used as tags in chemical compositions to unambiguously identify such compositions and to quantitatively determine the amounts of such tracers in admixture with other materials.

SUMMARY OF THE INVENTION

The present invention relates to tracer-containing chemical compositions which contain a chemical product and at least one perfluorocarbon tracer wherein the total amount of perfluorocarbon tracer present is less than about 800 ppb and each tracer is present in an amount less than about 500 ppb. The present invention also relates to the use of one or more perfluorocarbon tracers in chemical products for identifying such products and quantitatively determining the amounts of such tracers in admixture with other materials.

The tracer-containing compositions of the present invention are valuable because they provide an environmentally acceptable system of tracing products using tracers which are non-toxic, inert and do not interfere with the earth's ozone. In addition, the tracers are ideal for monitoring the contamination, adulteration and/or dilution of products since they are not visually detectable.

DESCRIPTION OF THE FIGURE

The FIGURE consists of a chromatogram in which perfluorodimethylcyclobutane, perfluoromethylcyclohexane, perfluorodimethylcyclohexane isomers and perfluorotrimethylcyclohexane isomers were each detected at 1 ppb levels in gasoline.

DESCRIPTION OF THE PREFERRED EMBODIMENTS

By adding at least one perfluorocarbon tracer to a product, it is possible to trace the product. By adding multiple perfluorocarbon tracers in differing amounts, a unique fingerprint is obtained which serves as a distinctive mark or identifier associated with a particular product thereby allowing for even more accurate tracing. As used herein, the term "trace" or "tracing" refers not only to the use of perfluorocarbon tracers for identification purposes, but also refers to the use of perfluorocarbon tracers for quantitatively determining the amounts of such tracers present in admixture with other materials in order to detect the degree of contamination, adulteration or dilution thereof. These chemical tracers are commonly referred to as "taggants" since they are used to label, code, or "tag" the material to be identified.

The tracer-containing chemical compositions of the present invention contain at least one perfluorocarbon tracer at a level of less than about 500 ppb (parts per billion) per tracer to "tag" the material. As used herein, the term "tracer-containing chemical composition" refers to any chemical product which has incorporated therein at least one perfluorocarbon tracer in an amount less than about 500 ppb per tracer. The term "chemical product" is generally taken to mean synthetic or naturally occurring organic and inorganic products such as silicone waxes, silicone oils or solvents. A preferred class of chemical products is the class of hydrocarbon products containing hydrogen and carbon (and optionally one or more heteroatoms such as nitrogen, sulfur, silicon or oxygen) which are commonly derived from petroleum feedstocks including gasolines, lubricants, waxes, greases, elastomers or plastics.

Throughout the specification, the term "perfluorocarbon tracer" or "perfluorocarbon compound" refers to a completely fluorinated compound consisting entirely of atoms of fluorine and carbon. This material is generally, but not necessarily, a liquid at ambient temperature and pressure. Perfluorocarbon compounds which are solids under ambient conditions are nevertheless rendered useful in the present process by dissolution, emulsification or dispersion in a suitable medium.

In the preferred embodiment of the present invention, more than one perfluorocarbon tracer is utilized. Preferably, the chemical composition contains from 2 to 10, inclusive, perfluorocarbon tracers. Even more preferably, the chemical composition contains from 3 to 6, inclusive, perfluorocarbon tracers.

The total amount of perfluorocarbon tracer added to the chemical composition is dependent upon the number of perfluorocarbon tracers utilized. In any event, the total amount of perfluorocarbon tracers utilized does not exceed about 800 ppb. Each individual perfluorocarbon tracer is present in an amount less than about 500 ppb. Preferably, the amount of each tracer utilized is less than about 250 ppb. Even more preferably, the amount is from about 10 ppt (parts per trillion) to about 100 ppb, most preferably from about 50 ppt to about 500 ppt. By utilizing such small levels of tracer, only 0.5 lbs of tracer per one billion gallons of chemical product is required, thereby making this an environmentally and economically attractive process.

When more than one perfluorocarbon tracer is included, the perfluorocarbon tracers are each present in the same amount or in any combination of differing amounts. Preferably, at least two of the perfluorocarbon tracers are present in different amounts. It is even more preferable if each of the perfluorocarbon tracers utilized is present in a different amount.

By using a variety of perfluorocarbon tracers in differing amounts, replication, intentional or otherwise, of the "tracer package" is made virtually impossible due to the degree of sophistication required to determine the different tracers utilized as well as the ratio of amounts of each tracer to one another. For example, a product may contain four tracers, A, B, C and D. These tracers are added in differing amounts to establish a specific ratio of one tracer to the other in the final product, e.g., a ratio of 10 ppb A : 20 ppb B : 30 ppb C : 40 ppb D.

Any perfluorocarbon tracer or mixtures of various perfluorocarbon tracers is utilized in the present invention. Preferably, the perfluorocarbon tracers utilized contain from 3 to 20 carbon atoms, inclusive, more preferably from 3 to 10 carbon atoms, inclusive. The perfluorocarbon tracers preferably have a boiling point of less than about 500° C. at 10 torr, more preferably less than about 300° C. at 10 torr. Examples of perfluorocarbon tracers which are used successfully in the process of the present invention include: perfluorocycloalkanes such as, perfluorodimethylcyclobutane, perfluoromethylcyclohexane, perfluorodimethylcyclohexane, perfluorotrimethylcyclohexane and perfluoromethylcyclopentane; perfluoroalkanes such as, perfluorohexane, perfluorododecane, perfluoropentane, and perfluorooctane; and mixtures thereof.

The perfluorocarbon tracer utilized is dependent upon the product being tagged. For instance, the preferred perfluorocarbon tracers for gasolines are perfluorodimethylcyclobutane, perfluoromethylcyclopentane, perfluoromethylcyclohexane and perfluorodimethylcyclohexanes, with perfluoromethylcyclopentane and perfluoromethylcyclohexane being the most preferred.

In many instances, the perfluorocarbon tracers are added directly to the chemical product. In some applications it is desirable to first dissolve, admix, disperse or emulsify the perfluorocarbon tracers in a liquid medium so that they will remain in solution in the final composition. The liquid medium utilized should be such that it does not react with the one or more perfluorocarbon tracers or the product to which the one or more perfluorocarbon tracers is added. The liquid medium will in many instances depend upon the product being tagged. Generally, the liquid medium is illustrated by ethanol, acetone, toluene, xylene, isooctane, mineral oils, petroleum ether, ligroin, gasoline, kerosene or mixtures thereof. Whenever emulsification or dispersion is necessary, any conventional emulsification or dispersion technique is suitable.

Once the perfluorocarbon tracers are included in the chemical composition, they may be used for different purposes. Specific tracers or mixtures of tracers are used to identify particular compositions. For example, tracers added to detergent additive packages which are subsequently injected into gasoline at distribution terminals allow downstream analysis for product identification. In addition, analysis of the product immediately after injection of the additive package will indicate whether or not a proper dosage of additive has been added. This is very appealing from the standpoint of the petroleum industry which can use such tracers to identify products or to detect theft. In addition, quantitative determination of the amounts of tracer present in admixture with other materials, including the ratios of one tracer to another, help to identify possible contamination, adulteration or dilution of chemical products. This is accomplished by comparing the perfluorocarbon tracers and their concentration in a possibly contaminated, adulterated or diluted product with those in a corresponding product which is known not to be contaminated, adulterated or diluted.

In practicing the process of the present invention, any analytical technique which provides sufficient selectivity to distinguish the perfluorocarbon tracer from other compounds in the sample, whether such other compounds are solvents used to prepare the samples for analysis, residues of the tagged material or contaminants, can be utilized. These techniques should be of sufficient sensitivity to detect the perfluorocarbon tracer when present in the sample at very low concentrations. The combination of conventional gas chromatographic separation and electron capture detection satisfies each of these requirements.

Preferably, a sample of the chemical composition to be tested is pre-treated prior to introduction into a gas chromatograph (GC) equipped with a standard electron capture detector (ECD) interfaced with a recorder. Pre-treatment consists of collecting the sample on activated carbon. The sample is then thermally desorbed and passed over a strong oxidizing catalyst, such as a 10%–25% $V_2O_5/Al_2O_3$ catalyst, thereby combusting non-perfluoronated material. The water is then removed from the combusted sample using a semi-permeable membrane prior to the combusted sample being introduced into the GC system.

The ranges and limitations provided in the instant specification and claims are those which are believed to particularly point out and distinctly claim the invention. It is, however, understood that other ranges and limitations that perform substantially the same function, in substantially the same way to obtain the same or substantially the same result are intended to be within the scope of the instant invention as defined by the instant specification and claims.

The invention will be further described by the following Illustrative Embodiment which is provided for illustrative purposes only and is not to be construed as limiting the invention.

Illustrative Embodiment

The perfluorocarbon tracers perfluorodimethylcyclobutane, perfluoromethylcyclohexane, perfluorodimethylcyclohexane and perfluorotrimethylcyclohexane were each dissolved in Indolene (an emission certification fuel available commercially from Amoco under the name Indolene Motor Fuel H.O. III) before being diluted in a gasoline sample to give a final concentration of 1 ppb per tracer. The gasoline sample containing the perfluorocarbon tracers was absorbed onto activated carbon before being thermally desorbed and passed over a 20% $V_2O_5/Al_2O_3$ catalyst to combust non-perfluoronated material. Water was then removed from the sample using a water semipermeable membrane before the sample was introduced into the gas chromatograph equipped with a standard electron capture detector. The FIGURE which consists of a chromatogram of the chromatographic analysis of the sample, indicates a variety of peaks which are labelled A–H. Table 1 discloses the perfluorocarbon tracer and retention time (minutes) which correspond to each of the labelled peaks. This analysis clearly indicates that multiple tracers, each in the ppb range, can be identified at the levels necessary for economical product tagging.

TABLE 1

| Peak | Tracer | Retention Time (minutes) |
|---|---|---|
| A | Perfluorodimethylcyclobutane | 1.52 |
| B | Perfluoromethylcyclohexane | 2.48 |
| C | Perfluorodimethylcyclohexane (ortho cis isomer) | 3.89 |
| D | Perfluorodimethylcyclohexane (meta trans isomer) | 4.49 |
| E | Perfluorodimethylcyclohexane (ortho trans isomer) | 4.84 |
| F | Perfluorodimethylcyclohexane (para trans isomer) | 5.28 |
| G | Perfluorotrimethylcyclohexane (major isomer 1) | 10.14 |
| H | Perfluorotrimethylcyclohexane (major isomer 2) | 10.72 |

What is claimed is:

1. A process for determining the possible adulteration of hydrocarbon products selected from the group consisting of gasolines, lubricants and greases comprising the steps of
   a) incorporating at least two perfluorocarbon tracers selected from the group consisting of perfluorocycloalkanes, perfluoroalkanes and mixtures thereof into hydrocarbon products in an amount less than about 500 ppb per perfluorocarbon wherein the total amount of perfluorocarbons is less than about 800 ppb to form tagged hydrocarbon products;
   b) analyzing a possibly adulterated tagged hydrocarbon product to determine the presence of perfluorocarbon tracers and the amount of each perfluorocarbon tracer present;
   c) comparing the perfluorocarbon tracers and the amount of each perfluorocarbon tracer found in the possibly adulterated tagged hydrocarbon product with the known perfluorocarbon tracers and amounts of each perfluorocarbon tracer in a corresponding tagged hydrocarbon product known to be unadulterated.

2. The process of claim 1 wherein from 2 to 10 perfluorocarbon tracers are present.

3. The process of claim 2 wherein from 3 to 6 perfluorocarbon tracers are present.

4. The process of claim 3 wherein each perfluorocarbon tracer is present in an amount from about 10 ppt to about 100 ppb.

5. The process of claim 2 wherein each perfluorocarbon tracer is present in an amount from about 10 ppt to about 100 ppb.

6. The process of claim 5 wherein each perfluorocarbon tracer is present in an amount from about 50 ppt to about 500 ppb.

7. The process of claim 5 wherein at least two of the perfluorocarbon tracers are present in different amounts.

8. The process of claim 4 wherein each perfluorocarbon tracer is present in a different amount.

9. A process for determining the possible adulteration of hydrocarbon products selected from the group consisting of gasolines, lubricants and greases comprising the steps of
   a) incorporating from three to six perfluorocarbon tracers selected from the group consisting of perfluorocycloalkanes, perfluoroalkanes and mixtures thereof into hydrocarbon products in an amount from about 10 ppt to about 100 ppb per perfluorocarbon wherein the total amount of perfluorocarbons is less than about 800 ppb to form tagged hydrocarbon products;
   b) analyzing a possibly adulterated tagged hydrocarbon product to determine the presence of perfluorocarbon tracers and the amount of each perfluorocarbon tracer present;
   c) comparing the perfluorocarbon tracers and the amount of each perfluorocarbon tracer found in the possibly adulterated tagged hydrocarbon product with the known perfluorocarbon tracers and amounts of each perfluorocarbon tracer in a corresponding tagged hydrocarbon product known to be unadulterated.

* * * * *